United States Patent [19]

Carolan et al.

[11] Patent Number: 5,750,279
[45] Date of Patent: May 12, 1998

[54] SERIES PLANAR DESIGN FOR SOLID ELECTROLYTE OXYGEN PUMP

[75] Inventors: Michael Francis Carolan; Paul Nigel Dyer, both of Allentown; Eric Minford, Laurys Station; Steven Lee Russek, Allentown, all of Pa.; Merrill Anderson Wilson, West Jordan, Utah; Dale M. Taylor, Salt Lake City, Utah; Brett Tamatea Henderson, Salt Lake City, Utah

[73] Assignee: Air Products and Chemicals, Inc., Allentown, Pa.

[21] Appl. No.: 240,054

[22] Filed: May 9, 1994

Related U.S. Application Data

[63] Continuation-in-part of Ser. No. 843,303, Feb. 28, 1992, Pat. No. 5,338,623.

[51] Int. Cl.$^6$ ..................................................... H01M 8/04
[52] U.S. Cl. .................................. 429/32; 429/38; 429/39
[58] Field of Search ................................... 429/32, 35, 38, 429/39

[56] References Cited

U.S. PATENT DOCUMENTS

| | | | |
|---|---|---|---|
| 4,197,362 | 4/1980 | Schmidberger et al. | 429/12 |
| 4,385,101 | 5/1983 | Catanzarite | 429/94 |
| 4,431,715 | 2/1984 | Isenberg | 429/30 |
| 4,490,445 | 12/1984 | Hsu | 429/32 |
| 4,648,945 | 3/1987 | Isenberg | 204/15 |
| 4,725,346 | 2/1988 | Joshi | 204/242 |
| 4,786,395 | 11/1988 | Otsuka et al. | 204/409 |
| 4,857,420 | 8/1989 | Maricle et al. | 429/32 X |
| 4,877,506 | 10/1989 | Fee et al. | 204/242 |
| 4,879,016 | 11/1989 | Joshi | 204/242 |
| 4,950,562 | 8/1990 | Yoshida et al. | 429/32 |
| 5,021,137 | 6/1991 | Joshi et al. | 204/242 |
| 5,034,288 | 7/1991 | Bossel | 429/32 |
| 5,045,169 | 9/1991 | Feduska et al. | 204/258 |
| 5,063,122 | 11/1991 | Rohr | 429/32 |
| 5,064,734 | 11/1991 | Nazmy | 429/33 |
| 5,209,989 | 5/1993 | Ishihara et al. | 429/38 X |
| 5,217,822 | 6/1993 | Yoshida et al. | 429/33 |
| 5,338,623 | 8/1994 | Nachlas et al. | 429/31 |
| 5,385,792 | 1/1995 | Shiratori et al. | 429/32 |

OTHER PUBLICATIONS

FIG. 5-1a, FIG 5-1b, "Fuel Cells", DOE/METC-86/0241, Technology Status Report, Morgantown Energy Technology Center, Morgantown, SW (1986) month unknown.

*Primary Examiner*—Stephen Kalafut
*Attorney, Agent, or Firm*—Keith D. Gourley

[57] ABSTRACT

An electrochemical device is disclosed comprising a plurality of planar electrolytic cells connected in series, each cell having an oxygen ion-conducting electrolyte layer, an anode layer and a cathode layer associated with the electrolyte layer, electrically conductive interconnect layers having gas passages situated therein for transporting gaseous streams, which interconnect layers electrically connect the anode layer of each electrolytic cell to the cathode layer of an adjacent planar cell, and sealing means positioned between the interconnect layers and the electrolytic cells to provide a gas-tight seal therebetween. The configuration of the interconnect layer and the placement of the seal means provides a separation between the seal and the conductive pathway of electrons between the anode layer and cathode layer which prevents corrosion or deterioration of the seal.

15 Claims, 8 Drawing Sheets

SERIES PLANAR DESIGN FOR SOLID ELECTROLYTE OXYGEN PUMP

RELATED U.S. APPLICATION DATA

This application is a continuation-in-part of U.S. patent application Ser. No. 07/843,303, filed on Feb. 28, 1992, now U.S. Pat. No. 5,338,623 the Specification which is incorporated by reference and made a part of this application.

FIELD OF THE INVENTION

This invention relates to solid-state electrochemical devices capable of transporting ions through an electrolyte. Specifically, this invention relates to an apparatus for transporting ions through series tubular structures and series planar structures which demonstrate improved electrical and pneumatic integrity.

BACKGROUND OF THE INVENTION

Conductive solids which transport ions, such as oxygen ions, are known in the art and are useful in many applications, including fuel cells, processes for producing, separating and purifying gases and gas sensing or monitoring. In certain applications, a series of electrolytic cells joined together provide increased electrochemical operation. An example of a series tubular system used as a fuel cell is disclosed in U.S. Pat. No. 4,431,715.

Efficient operation of series tubular or planar cells has been compromised in prior art systems by inherent weaknesses in system design and configuration. For example, individual electrolytic cells are commonly joined together by means generally known as an interconnect, which seals the cells together and provides an electrical connection between the cells. Such interconnects often fail over time as the seals degrade at elevated operating temperatures due to corrosion between the electrical conductor and the seal of the interconnect.

Effective seals are difficult to form between the components making up these devices. For example, when silver or silver alloy based electrodes are employed, the maximum temperature of the sealing material must be limited to the melting temperature of silver or silver alloy. Moreover, when glass is used as a sealing material, sufficient viscosity under operating temperature must be maintained in order to retain a seal over sustained periods of time. Further problems have been experienced in prior art cells which are connected in series due to limitations associated with manifolding the cells. Typical prior art interconnects often do not allow variation in configuration and manifolding of the electrolyte cells because of loss in pneumatic integrity experienced when operating such systems.

A solid electrolyte oxygen pump is presented in U.S. Pat. No. 4,877,506 which possesses electrodes which are shaped to form a plurality of linear, parallel channels on facing surfaces of the electrolyte. The air feed is directed into the channels formed of the air electrode and oxygen formed during operation of the device is removed by passage through the electrolyte via channels formed of the oxygen electrode or anode. A monolithic array is formed by stacking the cells with an interconnecting material between adjacent cells.

U.S. Pat. No. 4,490,445 discloses a solid oxide electrochemical energy converter which comprises alternating layers of solid oxide electrolyte plates and electrical conductor plates. Each electrolyte plate includes a coating of a porous oxidizer electrode on a first surface of the electrolyte and a coating of a porous fuel electrode on a second surface of said the electrolyte. Each conductor plate includes groove networks formed by ridges which define gas passages on both surfaces of the conductor plate, such ridges being in electrical contact with the electrode coatings on next adjacent electrolytes. Each conductor plate also possesses a means for tapping electricity from or introducing electricity into the converter. The conductor plates also possess circumferential ridges arranged along the edges of the conductor plate to define gas seals, the ridges being in contact with surface coatings on next adjacent electrolyte plates which surface coatings possess the same composition as that of the electrode coatings.

U.S. Pat. No. 5,217,822 discloses a solid oxide electrolyte fuel cell comprising a a solid electrolyte element composed of zirconia stabilized with yttria, a porous anode plate essentially composed of nickel and zirconia partly stabilized with magnesia, the anode plate having an integral portion serving as an anode, a porous cathode composed of lanthanum strontium manganite, a porous cathode plate composed of lanthanum strontium manganite and a separator composed of lanthanum chromite. The solid oxide electrolyte element, the cathode, the cathode plate and the separator are laminated on the anode plate in the enumerated order. The anode plate has formed on its surface opposite to the surface which contacts the solid electrolyte elements, a plurality of grooves in which a fuel gas flows. The cathode plate is also formed with a plurality of grooves in which an oxidizer gas flows on its surface facing the solid electrolyte element. After flowing in the grooves, the reaction gases pass through cavities in the electrode plates and are supplied to the solid electrolyte element.

Electrochemical systems having improved interconnects between the cells to assure electrical and pneumatic integrity of the system are desired in order to provide sealing integrity between the cells and to provide a series planar electrolytic cell system having simplified interconnection of the cells while permitting variation in manifolding and configuration.

SUMMARY OF THE INVENTION

In accordance with the present invention, the solid state electrochemical structure for transporting ions includes a plurality of tubular or planar electrolytic cells joined together in series with electrical conductor means configured to provide electrical interconnection between each tubular or planar electrolytic cell, and further includes sealing means for securing each electrical conductor to each contiguous tubular or planar cell with which each is associated to provide a pneumatic seal while permitting variation in manifolding and process configuration. Particular advantages are achieved when the planar cells are manifolded in a cross-flow configuration.

The electrochemical devices of the present invention can be used for a variety of processes including the separating of any ionizable component from a feedstream wherein such ionizable component is capable of being transported through the ionic conducting electrolyte layer. For example, the ionizable component may be oxygen present in air wherein oxygen ions are passed through the ionic conducting separation components comprising the electrochemical device. Hydrogen can also be separated from a feed stream by fabricating the ionic conducting electrolyte layer from a ceramic which is capable of transporting the ionized hydrogen species. These devices can also be readily adapted to function as partial oxidation devices wherein an oxygen-containing feedstream is introduced into one set of gas passages situated in the interconnecting layer of the device and a feedstock to be oxidized is introduced into the other set of gas passages whereby oxygen transported through the electrolyte layers is contacted with the feedstock to be oxidized.

Thus, the invention, as claimed, utilizes a first electrode and a second electrode. In the case wherein the ionic conducting electrolyte is chosen to conduct a negative ionic species such as in the case of separating oxygen from a oxygen-containing feedstream, the first electrode layer is the anode and the second electrode layer is the cathode. In the case wherein the ionic conducting electrolyte is chosen to conduct a positively charged ionic species such as in the case of separating hydrogen from a hydrogen-containing feedstream, the first electrode layer is the cathode and the second electrode layer is the anode.

The tubular cells of the electrochemical devices are generally cylindrical bodies having a thin wall with external and internal opposing surfaces. The tubular cells are adapted to receive gases therein, and each tubular cell is open at both ends thereby providing communication between the cells when the tubular cells are placed end to end. In an alternate embodiment, the electrochemical devices can be formed from a series of planar cells which are generally flat bodies having opposing surfaces, for convenience referred to as a first surface and a second surface. Each flat plate may have a thickness ranging from 10 µm to about 1 cm. A preferred thickness is from about 20 µm to about 1 mm. The electrolyte is non-porous in order to prevent escape of gas from within the cell. The flat electrolytic cells are adapted with structural elements to receive gases therein, and each cell possesses one or more openings to provide communication between the cells when one or more stacks are manifolded.

Suitable electrolytes for making the tubular or planar cells include oxygen ion conducting ceramic metal oxides such as zirconia, ceria, hafnia, bismuth oxide and the like or mixtures containing such oxides when oxygen ion transport is desired. Electrolytes of this type are disclosed in U.S. Pat. Nos. 4,725,346; 4,879,016; and 5,021,137. The ceramic used in the electrolytes may be doped with other materials, such as calcia, yttria or strontia. Electrolytes such as beta alumina, NASICON and the like may be used if sodium ion transport is desired.

An anode is associated with one surface of the tubular cell or flat plate, either the first surface or the second surface, while a cathode is associated with the opposing surface. In a particularly suitable tubular cell, the anode is in the form of a coating adhered to the inner surface of the tube and the cathode is in the form of a coating adhered to the outer surface. Each tubular cell of a multi-cell structure has the anode thereof associated with the same surface as every other tubular cell. In a particularly suitable planar cell, the anode is in the form of a coating adhered to the first surface of the plate and the cathode is in the form of a coating adhered to the second surface. Each planar cell of a multi-cell structure has the anode thereof associated with the same surface as every other planar cell.

The anode and cathode are porous or permeable to gas molecules thereby allowing gas to penetrate the electrode. Materials which are particularly suitable for use as electrodes (i.e. the cathode and anode) include silver, alloys of silver, composites of silver or silver alloys with one or more oxide ion-conductive materials. Such alloys preferably contain at least 50% silver. Metals which may be alloyed with silver or used instead of silver include palladium, platinum, gold and copper. In addition, some mixed conducting ceramic oxides may be used alone or in the form of composites with silver, including lanthanum strontium cobaltite, which is known to be particularly effective as an electrode for oxygen generation systems.

The anodic and cathodic materials may be applied to the respective surfaces of each tubular or planar cell by means known in the art. Such application methods include sintering of a paste material applied by screen printing or conventional coating techniques, plasma spraying or sputtering. The coating of electrode material on the electrolyte is substantially continuous, i.e. there are no spaces or breaks in the coating. The placement of the anode on one surface of the electrolyte is preferably coextensive with placement of the cathode on the opposing surface. The thickness of the anode or cathode on the ceramic electrolyte is generally between about 0.1 microns and about 100 microns, and preferably between about 1 to about 20 microns. The electrode layers are preferably thin in order to allow movement of gases freely therethrough. When very thin electrodes are used it may be desirable to use a current conductor, such as a metallic grid or a composite of the electrode with a silver coating applied over the electrode to minimize sheet resistance. From an ion transport standpoint, very thin electrolytes are preferred so long as the electrolyte possesses sufficient structural integrity. From a structural standpoint, thicker electrolytes may be required, especially if there is, or could be, a significant pressure differential across the electrolyte.

The tubular cells of the structure are connected end-to-end in series by electrical conductors, or interconnects. Aligning several tubular cells is more advantageous than using single long tubular cell because the electrons have a shorter distance to travel and sheet resistance is reduced accordingly. Further, lower power is required for an equivalent amount of oxygen production. Planar cells can be connected in series by stacking wherein the substantially flat cells are likewise connected electrically by such interconnects. Likewise, aligning several planar cells in a stack arrangement is more advantageous than employing a single long planar cell because sheet resistance is reduced accordingly.

The interconnects of the tubular and planar systems are configured to form an electrical connection between the anode of one cell and the cathode of an adjacent cell. The interconnects are formed of highly electrically conductive, substantially non-ionically conductive non-porous material which is preferably resistant to oxidation. The material used for the interconnects must also have a thermal expansion coefficient compatible with that of the material used to form the tubular or planar cells. Thus, when the tubular or planar cells expand under high temperature, the interconnects will similarly expand without damaging the individual cells or interconnects.

Examples of materials which may be used to form the interconnects include electrically conducting oxides like LSM (lanthanum strontium manganite), LSCr (lanthanum strontium chromite), LCM (lanthanum calcium manganite) and similar materials, and high chrome metal alloys such as Inconel® (600 series) (76% Ni, 15.5% Cr, 8% Fe) or stainless steel (400 series) and similar corrosion resistant metals. A particularly suitable material for the interconnect is $La_xSr_{1-x}MnO_3$ wherein x ranges from 0.2 to 0.7.

The interconnects are joined to the tubular or planar cells by sealing means which provide a gas-tight seal thereby preventing leakage of oxygen or other gases from within the tubular cells or between contiguous planar cells. Sealing means are formed between the electrolyte and the interconnect in a manner which provides a separation between the electrical pathway and the sealing means. Separation of the sealing means from the electrical pathway, in addition to the configuration of the interconnect, prevents deterioration of the seal resulting from high temperature operation of the electrochemical device.

The sealing means comprises a sealant material which provides a comprehensive, gas-tight barrier between specified components. For tubular cells, the sealing means provides a gas tight barrier between the feed and product gases and is situated between an end surface of the interconnect and the adjacent end surface of an electrolytic cell. For planar cells, the sealant is a gas tight barrier situated between two surfaces of an interconnect and adjacent cells in which case a comprehensive, gas-tight barrier is provided between the feed gas, product gas and the external environment.

The sealant material must also have a thermal expansion coefficient comparable to that of the interconnect material and the electrolyte. A particularly suitable sealant is a devitrified glass, i.e. a glass material which, after being melted and thermally treated, converts to a glass/ceramic upon cooling. An example of a suitable devitrified glass is a lithium alumino-silicate. Other examples of suitable sealants include glass, glass-ceramic composites, glass-metal composites, oxidation resistant metal alloys, brazes such as Ag/Pd alloys and the like.

In a first embodiment of the tubular system, an interconnect having a bell-shape is positioned between two tubular cells and communicating layers of conductive material join the anode of one cell to the interconnect and join the interconnect to the cathode of an adjacent cell to form an electron path between the electrodes via the interconnect. Sealant is placed relative to the interconnect and the tubular cells in a manner which forms a seal therebetween but is remote from the electrical pathway of the interconnect. The conductive material positioned between the electrode and the interconnect may be a conductive metal such as silver, a silver alloy, platinum or the like.

In an alternative embodiment of the tubular system, a collar of material is positioned around both ends of each tubular cell, and the interconnect is positioned between the collars of adjacent cells. Particularly suitable materials for the collars are oxidation-resistant ceramics, such as ceria or calcia doped ceria, which have a thermal expansion coefficient which is compatible with that of the electrolyte with which the collars are associated. The material used for the collars may also be ion-conducting. Other suitable materials include any inert material which has a thermal expansion coefficient comparable to that of the electrolyte, such as stainless steel or forsterite (a composite magnesium silicate oxide). The collars may be secured to the ends of the tubular cells by co-sintering or by applying a high temperature material such as aluminosilicate glass. Sealant is then positioned between the collars and the interconnect to effect a gas-tight seal. This embodiment provides a configuration with less restrictive tolerances in registration between the tubular cells and the interconnect creating a stronger, more reliable seal.

The geometrical configuration of the interconnects permits manifolding or stacking of numerous tubular or planar cells while maintaining electrical and pneumatic integrity of the system. End caps and coupling structures are provided as appropriate for the integration of a series of tubular or planar cells. The end caps have slightly different purposes in the tubular tacks and planar stacks. In tubular stacks, the end caps merit gas connections to be made to the stack in addition to electrical connection. In planar stacks, the end caps only serve to allow electrical connections to be made. The end caps are made from conductive materials as described previously in connection with the interconnects.

Coupling structures are secured between the negative end cap of one series of tubular cells and the positive end cap of another series of tubular cells. The coupling structure forms an electrical connection between the separate series of electrolytic cells, and communicates gases between adjacent series of cells. The coupling structure is formed to the end caps in a manner which provides a gas-tight seal.

In a first embodiment of the planar system, an electrically conducting interconnect layer having gas passages formed on its surfaces is positioned between two planar electrolytic cells. Communicating layers of conductive material join the anode layer of one cell to the first surface of the interconnect layer, and join the second surface of the interconnect layer to the cathode layer of an adjacent cell thereby forming an electron path between the electrodes via the electrically conducting interconnect layer. Sealant is placed relative to the interconnect layers and the planar cells in a manner which forms a seal therebetween but is remote from the electrical pathway of the interconnect layer. The conductive material positioned between the electrode layers and the interconnect layer may be a conductive metal such as silver, a silver alloy, platinum, a paste of the electrode or interconnect materials, and the like.

The planar system can be configured to allow for a variety of manifolding or stacking arrangements while maintaining electrical and pneumatic integrity of the system. End plates and coupling structure are provided which, when placed at the end of a series of planar cells, permits stacking, or aggregation, of numerous planar cells. There is provided a positive end plate which forms an electrical connection with the anode of a terminal planar cell, and a negative end plate which forms an electrical connection with the cathode of a terminal planar cell. The end plates are made from electrically conductive materials as described previously in connection with the interconnect layers and may have gas passages on the surfaces adjacent to the electrode layers. The end plates are formed to the ends of the planar cells as described with respect to the interconnect layers and sealing means are positioned to provide a pneumatic seal.

BRIEF DESCRIPTION OF THE DRAWINGS

In the drawings, which illustrate what is currently considered to be the best mode for carrying out the invention.

DETAILED DESCRIPTION OF THE INVENTION

Figure 1:
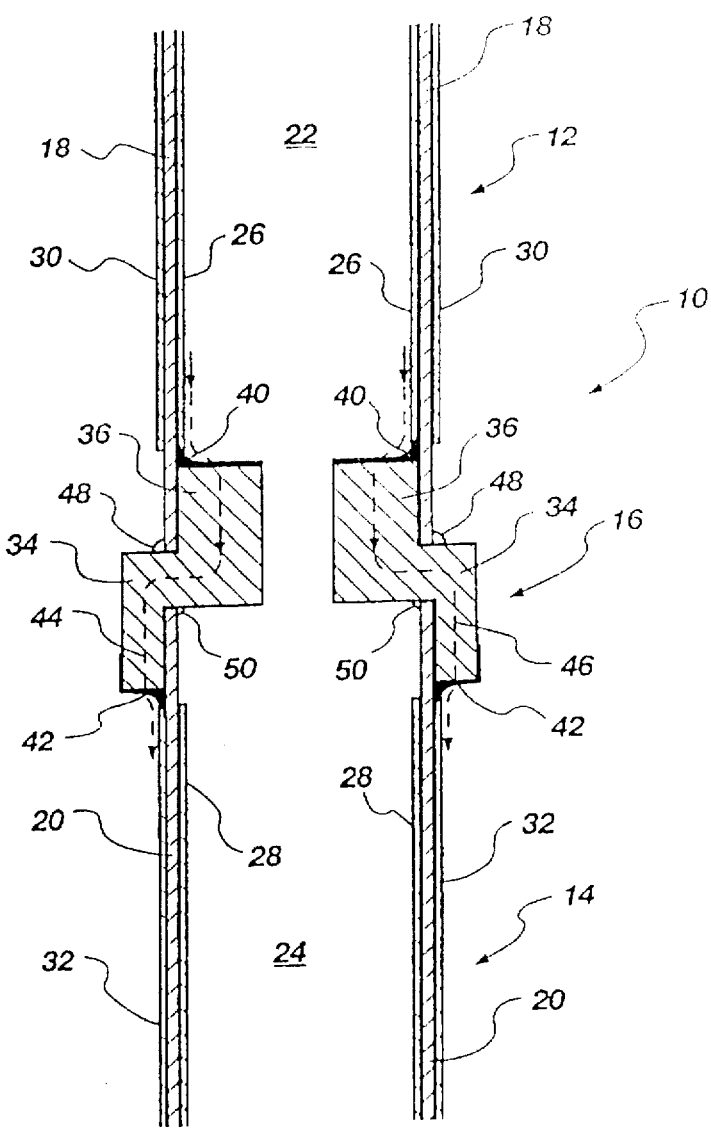
FIG. 1 is a view in longitudinal cross section illustrating the interconnect positioned between a first tubular cell and a second tubular cell.

As shown by FIG. 1, the electrochemical structure 10 of the invention includes a plurality of electrolytic cells 12, 14 joined together by a bell-shaped interconnect 16. The electrolytic cells 12, 14 are cylindrical tubes having walls 18, 20 which form the electrolyte. The walls 18, 20 form an internal space 22, 24 within which gases are formed during operation of the electrochemical structure 10. A suitable material for forming the cells 12, 14, and thus the electrolyte 18, 20, is ceria. The walls 18, 20 of the electrolytic cells 12, 14 range from about 0.1 to 5 mm in thickness.

The anodes and cathodes of the electrochemical structure may be formed from the same or different materials. For example, an anode 26, 28 is formed to the interior surface of the concentric wall 18, 20 of the cells 12, 14. The anode 26, 28 is a coating of LSCO (lanthanum strontium cobaltite) with an intermediate coating of LSCO and silver applied to the wall 18, 20. The coating can be attached by sintering of a paste or by sputtering, a technique well known in the art. The thickness of the LSCO-silver anode 26, 28 is about 20 microns.

A cathode 30, 32 is formed to the exterior surface of the concentric wall 18, 20 of the cells 12, 14. The cathode 30, 32 is a coating of LSCO placed on the electrolyte with an intermediate coating thereover of LSCO silver alloy having at least 50% silver as a component thereof. The cathode 30, 32 is formed to the wall 18, 20 in a manner similar to that of the anode 26, 28. The thickness of the cathode material is about 20 microns. The coating of the anode 26, 28 on the interior surface of the wall 18, 20 is coextensive with the coating of the cathode 30, 32 on the exterior surface of the wall.

Figure 2:
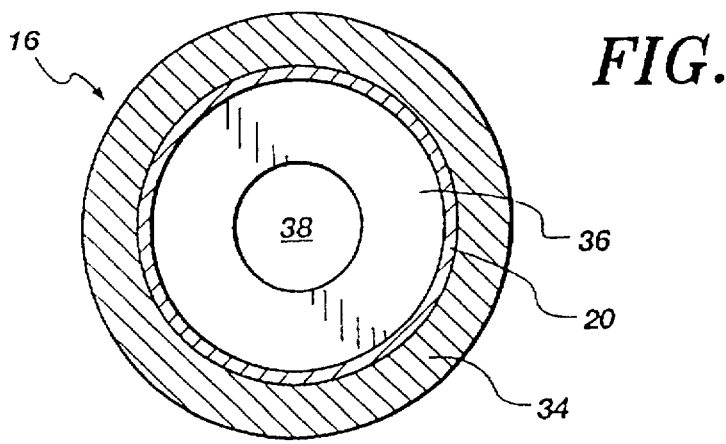
FIG. 2 is a view in cross section of the interconnect taken at line A—A in FIG. 1.

Adjacent tubular electrolytic cells 12, 14 are joined together by an interconnect 16. As illustrated in FIG. 2, the bell-shaped interconnect 16 is circular having an outer cap 34 and an inner sleeve 36. The outer cap 34 is sized to surround and receive the end of one tubular cell 14 and to come into registration with the exterior surface of the wall 20 of that tubular cell 14. The inner sleeve 36 is sized to fit within and register against the interior surface of the wall 18 of an adjacent tubular cell 12. A central void 38 provides communication between the interior 22 of one tubular cell 12 and the interior 24 of the adjacent tubular cell 14.

As illustrated by FIG. 1, the inner sleeve 36 of the interconnect 16 is adjacent the anode 26 of tubular cell 12. A conductive material 40, such as silver or silver alloy, is formed between the anode 26 and the interconnect 16. Similarly, the outer cap 34 of the interconnect 16 is adjacent the cathode 32 of tubular cell 14, and a conductive material 42 is formed between the interconnect 16 and the cathode 32. The conductive material 40, 42 serves to direct electrons from the anode 26 to the interconnect 16, and from the interconnect 16 to the cathode 32. The pathway which the electrons travel is indicated by the broken arrows 44, 46.

To effect a pneumatic seal between the tubular cells 12, 14 and the interconnect 16, sealing means in the form of a sealant are positioned therebetween. That is, a sealant 48 of devitrifying glass is formed about the interconnect 16, where the end of the tubular cell 12 meets the outer cap 34, by placement of a bead of glass material thereabout. The bead is then heated to melt the material. The devitrified glass material has a melting point less than that of the silver or silver alloy electrodes, and heating of the sealant to form the seal does not affect the electrode material. Upon cooling, the devitrifying glass turns to a glass/ceramic. A similar bead of devitrifying glass sealant 50 is positioned between the interior surface of the adjacent tubular cell 14 and the interconnect 16, and is heated and cooled to form a gas-tight seal.

It is notable that the sealant 48 on the exterior of the interconnect 16 is positioned so that it is separated from the electron pathway of the interconnect 16. Likewise, the sealant 50 on the interior of the interconnect 16 is separated from the electron pathway of interconnect 16. By the positioning of the sealing means, the seals are spaced apart from the interconnect and also preferably from the electrodes in a manner which prevents corrosion of the sealing means when the electrochemical cell is operating at high temperatures.

The electrochemical cell is produced by first applying a coating of LSCO to both the interior and exterior surfaces of the tube. The tubes are then fired to about 1120° C. An intermediate coating of a mixture of LSCO and silver palladium alloy is then placed on the LSCO coatings of the interior and exterior surfaces of each tube. A particularly suitable composition for the intermediate coating is about 75% LSCO to about 25% silver-palladium alloy. The ratio of silver to palladium in the alloy may vary, but a ratio of 70% to 30% is suitable. The intermediate coating is fired to both surfaces of the tubes at about 1120° C. A coating of silver is then placed on the interior surface of each tube to form current collector means on the anode 26, 28 of each tube. The silver coating is fired at about 750° C.

The tubes are then joined end-to-end by attachment of the interconnects. The interconnects are formed to tubes by application of the devitrifying glass, and the tubes are fired at about 940° C. A silver coating is then placed on the exterior surface of each tube to provide a current collector means on each cathode. The interconnected tubes are fired again at 750° C. The formation of the silver coating on the cathode, following application and firing of the devitrified glass, is particularly important to operation of the electrochemical cell since firing of the silver coating on the cathode at high temperatures, if applied before the application and firing of the devitrified glass, would degrade the performance of the current collector.

Figure 3:
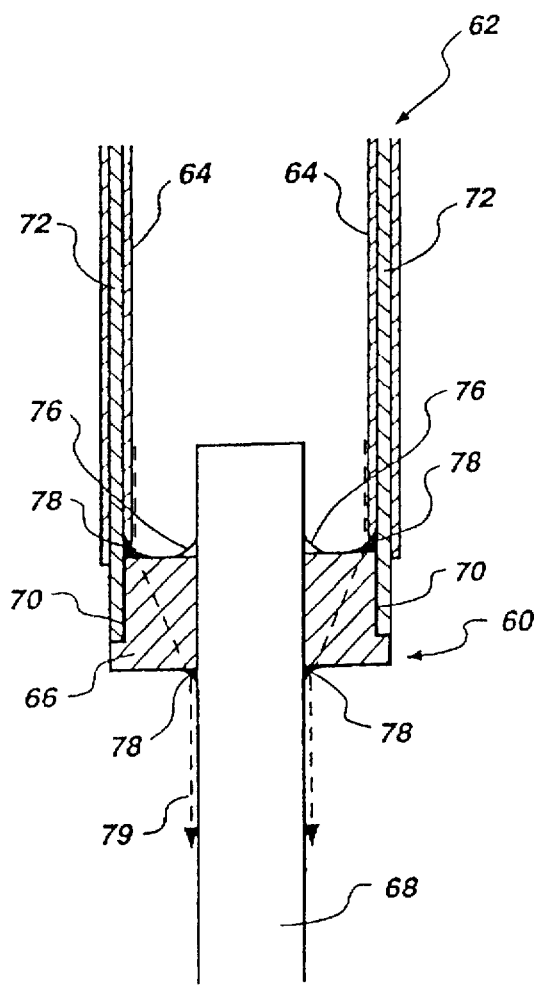
FIG. 3 is a view in longitudinal cross section of a positive end cap of the invention.
Figure 4:
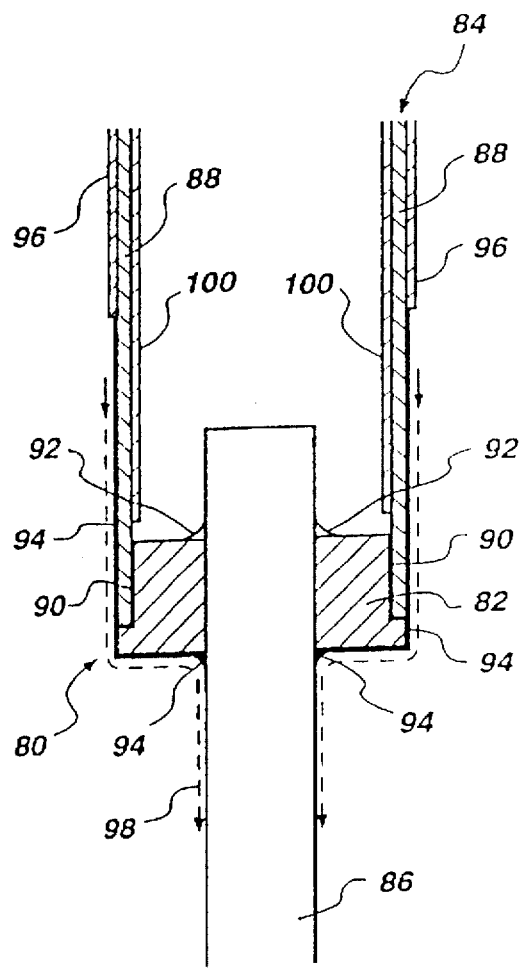
FIG. 4 is a view in longitudinal cross section of a negative end cap of the invention.
Figure 5:
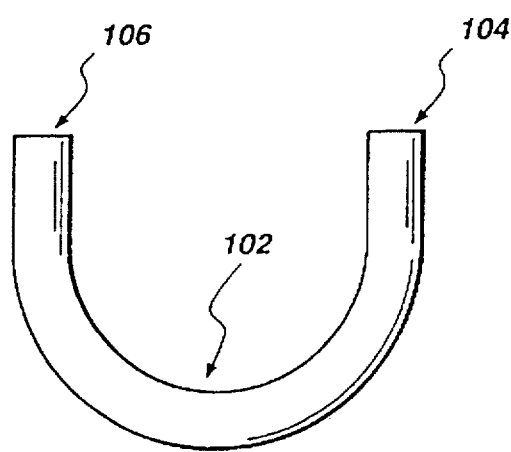
FIG. 5 is a plan view of a coupling structure.

In operation, an electrical current is applied to the electrodes at the beginning tubular cell of the series. Electrons flow from the anode on the inner surface of a tubular cell, through the pathway of the interconnect, and to the cathode of the adjacent tubular cell. When the series tubular system is used, for example, in the production of oxygen gas, air or other oxygen-containing gas surrounds the outside of the tubular cells. Electrons at the cathode ionize oxygen atoms to oxygen ions. The oxygen ions pass through the electrolyte via the influence of a voltage differential into the interior of the tubular cell where the electrons are given up to the anode and oxygen atoms are formed inside the tubular cells. The electrons given up at the anode continue to travel through the interconnect and to the cathode of an adjacent cell where the process continues at that cell. The reaction to form oxygen atoms can be expressed as cathode $O_2 + 4\ e^- \rightarrow 2O^{2-}$ anode $2O^{2-} \rightarrow O_2 + 4\ e^-$ A plurality of tubular cells joined in series can be further joined to another plurality of tubular cells joined in series to provide an integrated system of interconnected electrolytic cells. End caps and coupling structure, as illustrated in FIGS. 3, 4 and 5, are used to join separate series of tubular cells together. A positive end cap 60, as shown by FIG. 3, is attached to one end of a tubular cell 62 to direct electrons from the anode 64. The positive end cap 60 comprises a cap 66 which inserts into the end of the tubular cell 62. The cap 66 is formed of the same materials as previously described in connection with the interconnect, namely a highly conductive, oxidation resistant material having a thermal expansion comparable to that of the tubular cell material. A particularly suitable material is LSM ($La_{0.5}Sr_{0.5}MnO_3$). Through the positive end cap 66 is positioned a hollow conduit 68 of stainless steel 446.

The end cap 60 is joined to the tubular cell 62 by sealing means to pneumatically seal the system. Sealant 70, such as a devitrified glass, is positioned between the electrolyte 72 and the cap 66. The sealant 70 is heated and then cooled as described previously in connection with sealing of the interconnect. A bead of sealant 76 is also positioned between the hollow conduit 68 and the cap 66, interior to the tubular cell 62. The sealant 76 is melted and then cooled to form a gas-tight seal around the hollow conduit 68. The sealant 70, 76 is positioned to be separated from the conductive pathway of electrons traveling through the cap 66.

A bridge of electrically conductive material 78 is formed between the anode 64 and the cap 66 on the interior surface of the tubular cell 62. Electrically conductive material 78 is also formed between the cap 66 and the hollow conduit 68 on the exterior surface of the end cap 60. The electrically conductive material is that as described above in connection with the interconnect, namely silver, silver alloys, platinum and the like. The conductive material 78 directs electrons from the anode through the cap 66 and to the hollow conduit 68, as indicated by the broken line 79. The hollow conduit 68 is also completely coated on the outer surface with silver. Although conductive ceramic oxides could be used as conductive material 78, metals are usually preferred because they are more malleable, especially at elevated temperatures.

The negative end cap 80, as shown in FIG. 4, also comprises a cap 82 which inserts into the end of a tubular cell 84 and a hollow conduit 86 positioned through the cap 82. As with the positive end cap 60 and the interconnects, the cap 82 is formed of a highly conductive, oxidation-resistant material which has a thermal expansion rate comparable to that of the tubular cell material. A particularly suitable material is LSM ($La_{0.5}Sr_{0.5}MnO_3$). The hollow conduit 86 is made from a conductive material, preferably stainless steel 446.

The cap 82 is sealed to the electrolyte 88 of the cell 84 by placement of a sealant 90 therebetween. A bead of sealant 92 is also positioned between the cap 82 and the hollow conduit 86. The sealants 90, 92 are preferably devitrifying glass as described previously. The sealant is heated and then cooled to form a gas-tight seal between the end cap 80 and the tubular cell 84. The sealants 90, 92 are positioned to be separated from the conductive pathway of electrons.

Conductive material 94, suitably silver, silver alloys, platinum and the like, is applied to the outside of the tubular cell 84 and extends from the cathode 96, over the end cap 82, to the hollow conduit 86 and over the conduit 86. The conductive material 94 thus provides an electrical pathway for electrons to travel between the cathode 96 and the hollow conduit 86, as indicated by the broken line 98. It should be noted that the anode 100 of the tubular cell 84 does not contact the cap 82, as illustrated in FIG. 4, to avoid short circuiting of the cell.

Figure 6:
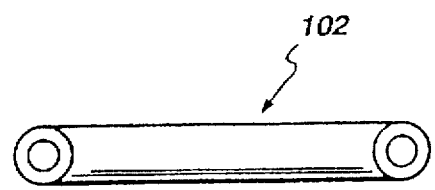
FIG. 6 is a view in cross section of the coupling structure shown in FIG. 5, taken at line B—B thereof.

Separate series of interconnected tubular cells may be formed together with a coupling structure 102, as shown in FIGS. 5 and 6. The coupling structure 102 may take any expedient shape or configuration, but is illustrated as a U-tube. One end 104 of the coupling structure 102 is connected to the positive end cap secured to the terminal cell of a first series of cells, and the other end 106 of the coupling structure 102 is connected to the negative end cap secured to a terminal cell of a second series of cells. The coupling structure is formed of a highly conductive, oxidation-resistant material. Suitable materials include Inconel® and stainless steel. A particularly suitable material is stainless steel 316L.

The coupling structure 102 may be joined to the end caps by any suitable means, including welding, brazing, soldering, or the like. A particularly suitable means of joining the structures is silver brazing using a silver alloy brazing material containing copper, zinc, cadmium or similar material. A particularly suitable brazing material contains 45% silver, 30% copper and 25% zinc. Such alloys maintain efficient electrical conductivity in the area of the seal while providing a pneumatic seal. As shown by FIG. 6, the coupling structure 102 is hollow to provide communication of gases between a first series of tubular cells and a second series of cells. After brazing, if an electrical connection is required between a first and second series of tubular cells, then the U-tube may be coated with silver or silver alloy.

Figures 7, 8:
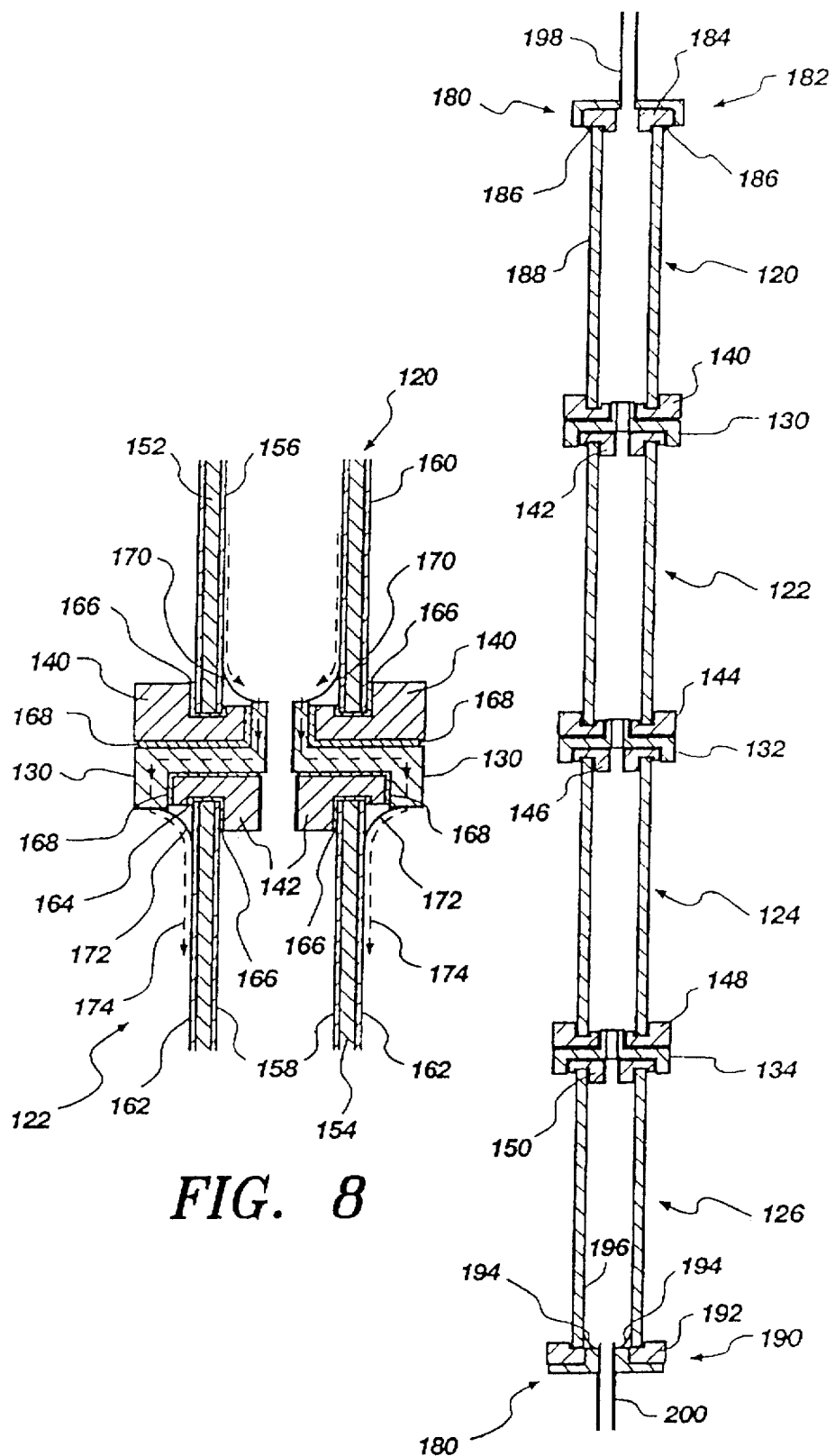
FIG. 7 is a view in longitudinal cross section of a series of interconnected cells illustrating an alternative embodiment of the invention.
FIG. 8 is an enlarged view of the interconnect illustrated in FIG. 7.

In an alternative embodiment, as illustrated by FIGS. 7 and 8, tubular electrolytic cells 120, 122, 124, 126 are joined together by interconnects 130, 132, 134 as previously described, except that collars 140, 142, 144, 146, 148, 150 are associated with the ends of each tubular cell 120, 122, 124, 126 which interface with the interconnects 130, 132, 134. Collars 140, 142, 144, 146, 148, 150 associated with the ends of the tubes provide greater sizing tolerances between the tubular cells and the interconnects, and simplify sealing the cells to the interconnects. The integrity of the seal is also increased as a result of increased sealing area.

As more clearly illustrated in FIG. 8, a first electrolytic cell 120 is joined to a second electrolytic cell 122 with an interconnect 130. The electrolytic cells 120, 122 are cylindrical, and the wall forms the electrolyte 152, 154 of the cells 120, 122. An anode 156, 158 is formed to the inner surface of the electrolyte 152, 154, and a cathode 160, 162 is formed to the exterior surface of the electrolyte 152, 154 by application of a coating of LSCO and an intermediate coating of LSCO-silver alloy, as previously described. A silver coating is then applied to the interior surface of each cell at previously described.

Collars 140, 142 are associated with the ends of the electrolytic cells 120, 122. The collars 140, 142 are typically made of the same ceramic material of which the electrolyte is made. The collars thus have a comparable thermal expansion rate as the electrolyte. The collars are constructed of an oxidation-resistant material such as zirconia, hafnia, bismuth oxide, ceria or similar materials. Ceria is particularly suitable. Ceria and other ceramics may also be doped with various materials, such as calcia. The material of the collars 140, 142 may or may not be the same as that from which the electrolytic cell is produced. It is important that the material of the collar has a thermal expansion rate comparable to that of the electrolytic cell material. The collars 140, 142 are annular disks having a groove 164 formed therein sized to receive the end of a cell. There need not be a close fit between the groove 164 and the end of the cell 122.

As illustrated, the collar 140, 142 may be secured to the end of the cell 120, 122 by placing a sealant 166 therebetween. The sealant 166 is a material which will maintain the seal under high temperature operating conditions. Particularly suitable materials are high temperature glasses such as aluminosilicate glass, for example, lithium aluminosilicate. Alternatively, the collars 140, 142 may be sintered to the ends of the cells 120, 122 by techniques known in the art. The collars 140, 142 are then sealed to the interconnect 130 by means of a sealant 168 such as devitrifying glass.

A silver coating which acts as a current collector is applied to the exterior surface of each tube, on the cathode, and is fired at 750° C., as previously described. Conductive material 170 is applied between the anode 156 of one electrolytic cell 120, the collar 140 and the interconnect 130 to effect a conductive pathway for electrons therebetween. Conductive material 172 is also applied between the interconnect 130, the collar 142, and the cathode 162 of the adjacent electrolytic cell 122 to complete the conductive pathway between the anode 156 and cathode 162 of adjacent cells. The pathway travelled by electrons is indicated by the broken line at 174. The conductive material 170, 172 is a highly conductive material such as silver or silver alloy.

Figure 9:
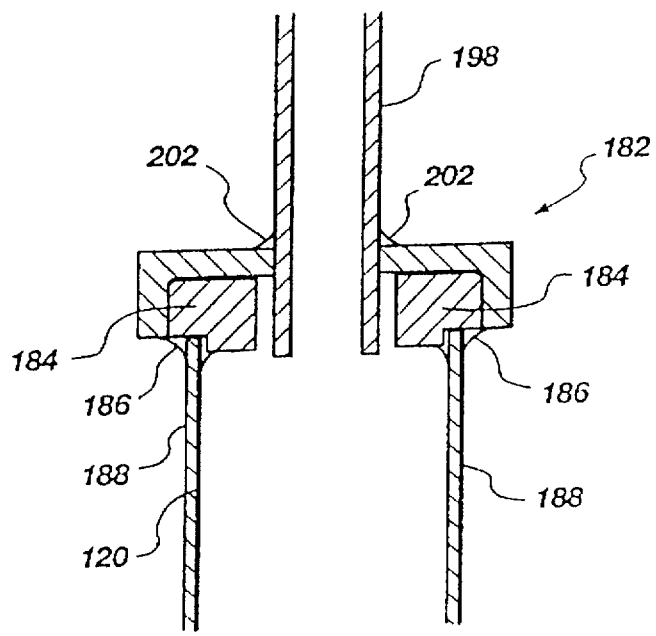
FIG. 9 is an enlarged view of a negative end cap illustrated in FIG. 7.
Figure 10:
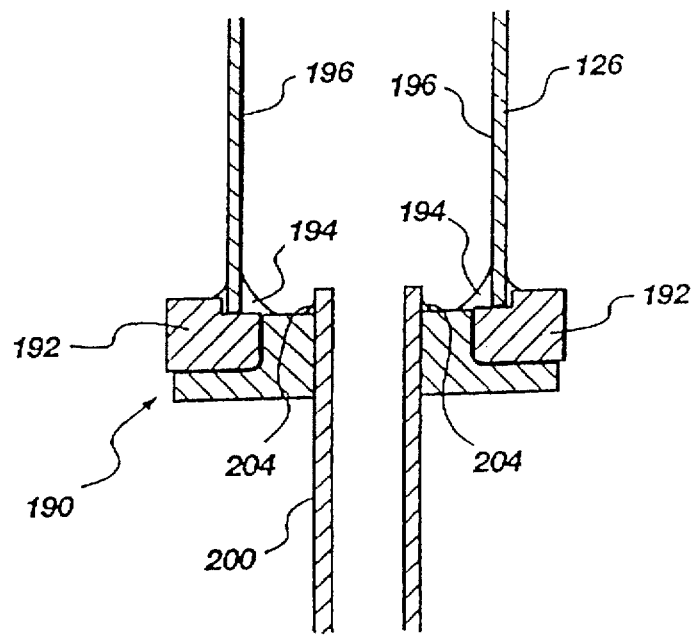
FIG. 10 is an enlarged view of a positive end cap illustrated in FIG. 7.

Referring to FIGS. 7, 9 and 10, a plurality of series tubular cells 120, 122, 124, 126 can be formed together by means of end caps 180 connected to the terminal cells 120, 126 of a series. A negative end cap 182 as shown in FIG. 9 is sealed to a ceria collar 184 of a first terminal cell 120 by sealant means as described previously. Conductive material 186 is positioned between the end cap 182, collar 184 and the cathode 188 of the cell 120. A positive end cap 190 as shown in FIG. 10 is sealed to the collar 192 of a second terminal cell 126 by sealing means previously described. Conductive material 194 is positioned between the end cap 190, the collar 192 and the anode 196 of the cell 126 to effect a pathway for electrons therebetween.

The material used for the end caps 180 of this embodiment is the same as described above in connection with the embodiment shown in FIGS. 1–6. Similarly, hollow conduits 198, 200 extend from the end caps 180 to provide communication of electrons and gases between integrated series of hollow conduit 198, 200 by either welding 202, 204, press fitting or the like.

Figure 11:
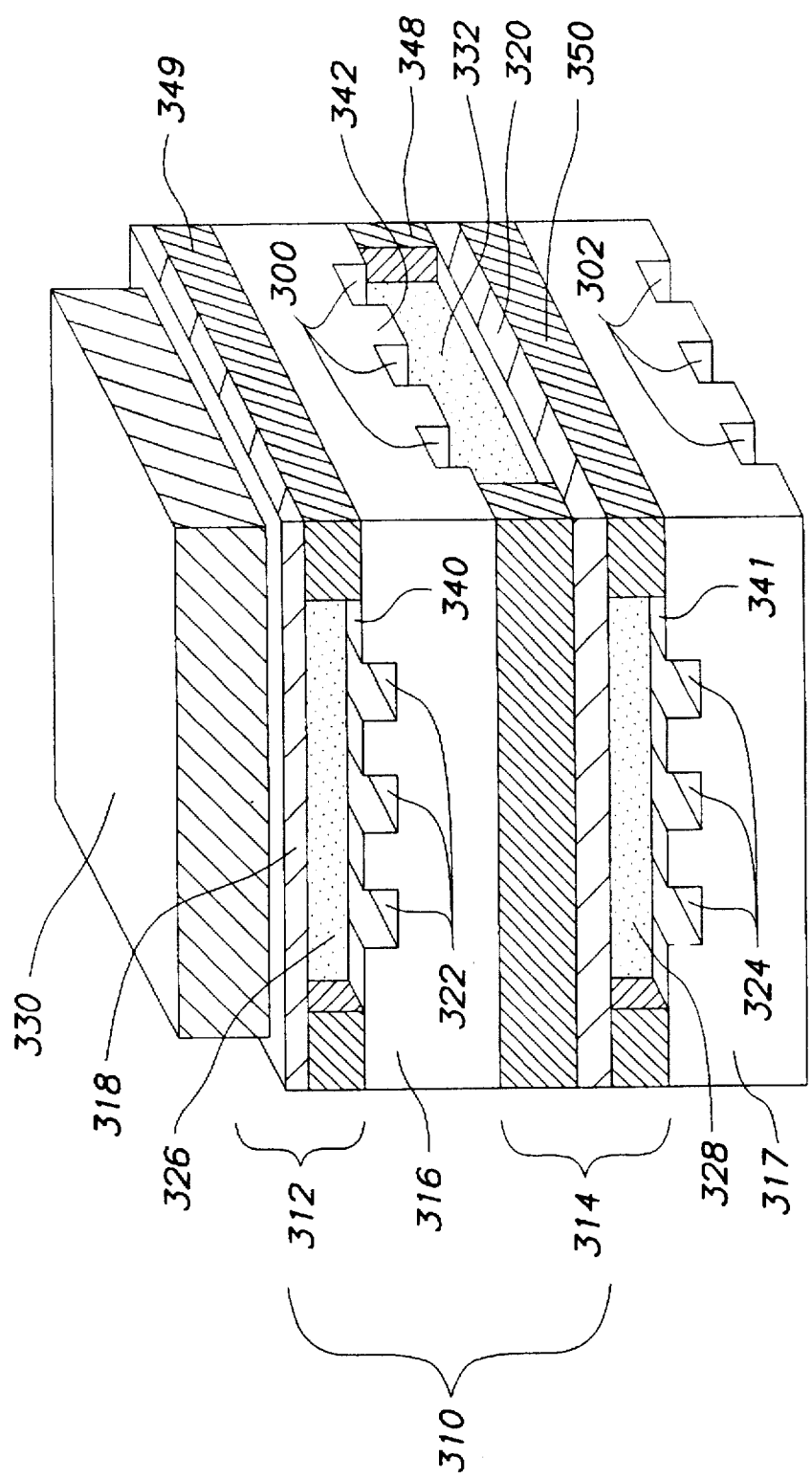
FIG. 11 illustrates an electrochemical structure comprising a first planar cell and a second planar cell which are joined in series by an interconnect positioned between such first planar cell and the second planar cell.

FIG. 11 presents an alternate embodiment of the present invention wherein a plurality of planar solid electrolyte cells are integrated in a series configuration. As shown in FIG. 11, the electrochemical structure 310 of the invention includes a plurality of electrolytic cells 312, 314 joined together by an electrically conducting interconnect layer 316. Interconnect layer 317 would likewise to used to join electrolytic cell 314 and another electrolytic cell or would form the terminus of the device via an end cap (not shown). The electrolytic cells 312, 314 consist of ion conducting electrolyte layers 318 and 320 having a first surface and a second surface. The ion conducting electrolyte layers 318, 320 of the electrolytic cell 312, 314 are about 5 µm to 1 mm thick.

The electrolyte layers 318, 320 may be formed of the same materials used in the tubular design embodiment and are preferably formed from a multicomponent ionic conducting metallic oxide comprising an oxide of at least two different metals or a mixture of at least two different metal oxides wherein the multicomponent metallic oxide demonstrates ionic conductivity at device operating temperatures, typically greater than about 500° C. Such ionically conducting multicomponent metallic oxides are represented by the formula $A_xA'_{x'}A''_{x''}O_z$, where A,A',A" may be independently selected from Groups 2, 3, 13, 14 and 15, the F block lanthanides and the D block transition metals according to the Periodic Table of the Elements adopted by the IUPAC wherein $0<x\leq1$, $0<x'\leq1$, $0\leq x''\leq1$, $x+x'+x''=1$ and z is a number which renders the compound charge neutral. A representative example is $Y_{0.182}Zr_{0.818}O_{1.909}$ which has an oxygen ionic conductivity of 0.1 ohm$^{-1}$cm$^{-1}$ at 1000° C. and an ionic transport number (the ratio of the ionic conductivity to the total conductivity) of close to 1. Other examples include $Sr_{0.1}Ce_{0.9}O_{1.9}$ and $Bi_{0.875}V_{0.125}O_{0.687}$.

Anode layers 326, 328 are formed to the first surface of the electrolyte layers 318, 320 of the cells 312, 314. The anode layers 326, 328 can be formed from an oxidation-resistant metal, an alloy or a multicomponent mixed conducting oxide represented by the formula $A_xA'_{x'}A''_{x''}B_yB'_{y'}B''_{y''}O_{3-z}$, where A,A',A" are chosen from the group comprising Groups 1, 2 and 3 and the F block lanthanides; and B,B',B" are chosen from the D block transition metals according to the Periodic Table of the Elements adopted by the IUPAC wherein $0<x\leq1$, $0\leq x'\leq1$, $0\leq x''\leq1$, $0<y\leq1$, $0\leq y'\leq1$, $0\leq y''\leq1$, $x+x'+x''=1$, $y+y'+y''=1$ and z is a number which renders the compound charge neutral, or a metal (or alloy) or a mixture of the two. For example the anode layers 326, 328 can be formed from $La_xSr_{1-x}CoO_{3-z}$ wherein x ranges from 0.2 to 1.0 and z is a number which renders the compound charge neutral (lanthanum strontium cobaltite or LSCO) with an intermediate coating of lanthanum strontium cobaltite and silver or silver-palladium alloy is applied to the first surface of the electrolyte 318, 320. The coating can be attached by sintering of a paste, applied, for example, by screen printing or by sputtering, or other techniques well known in the art. The thickness of the anode 326, 328 is about 0.1 to 100 microns.

Cathode layers 330, 332 are formed to the second surface of electrolyte layers 318, 320 of the cells 312, 314. Cathode layers 330, 332 may comprise a coating of an oxidation-resistant metal, an alloy or a multicomponent mixed conducting oxide according to the previously described formula. For example, LSCO may be placed on the electrolyte with an intermediate coating thereover of LSCO-silver alloy, such alloy having at least 50% silver as a component thereof. Cathode layers 330, 332 are formed to the second surface of electrolyte layers 318, 320 in a manner similar to that of anode layers 326, 328. The thickness of the cathode material is about 0.1 to 100 microns. The coating of anode layers 326, 328 on the first surface of electrolyte layers 318, 320 is coextensive with the coating of cathode layers 330, 332 on the second surface of the electrolyte layer.

Particularly suitable materials for fabricating the anode layer and cathode layer of this planar embodiment include lanthanum strontium cobaltite, lanthanum strontium cobalt ferrite, lanthanum barium cobaltite, strontium cobalt ferrite and lanthanum barium cobalt ferrite. Alternately, the cathode and anode layers may additionally contain silver or an alloy of silver.

Adjacent electrolytic cells 312, 314 are joined together by an interconnect layer 316. The interconnect layer 316 is made of an oxidation resistant material having a thermal expansion coefficient comparable to electrolyte layers 318, 320, a high electronic conductivity and low ionic conductivity. The material can be a multicomponent, electronically conducting oxide of the composition previously described, a metal or alloy, or a mixture of the two. Suitable electronically conducting oxides include lanthanum strontium manganite, lanthanum strontium chromite, lanthanum calcium manganite and lanthanum calcium chromite. Channels are formed, e.g., by pressing or layering tapes, in the second surfaces of the interconnects. Gas passages 322, 324 are formed between the first surface of the interconnect and the adjacent anode 326, 328, and serve to collect the product oxygen. Gas passages 300, 302 are formed between the second surface of the interconnect layer and the adjacent cathode layer 332 and serve to introduce the feed oxygen-containing gas to the device.

The respective gas passages for introducing the feed gas into the device and the gas passages for collecting the oxygen product or other gaseous product can be configured in a fashion to accommodate the manifolding desired for a particular application. Preferably, the respective gas passages are configured such that the passages for introducing the oxygen-containing gas run in a direction substantially perpendicular to the gas passages employed to collect the oxygen produced in the device. Thus, manifolds can be conveniently attached to one, two or more cells. Alternately, the respective gas passages are configured such that the passages for introducing oxygen-containing gas run in a direct substantially parallel to the gas passages employed to collect the oxygen product thereby allowing co-current or counter-current flow schemes. Of course, the orientation of the respective gas passages can be varied between such extremes.

As illustrated by FIG. 11, the first surface of the interconnect layer 316 is adjacent the anode layer 326 of cell 312. A conductive material 340, 341 such as silver or silver alloy or the material of the anode layer or interconnect layer, may optionally be formed between the anode layer 326 and the interconnect layer 316 and anode layer 328 and the interconnect layer 317. Similarly, the second surface (not shown) of the interconnect layer 316 is adjacent the cathode layer 332 of cell 314, and a conductive material 342 may optionally be formed between the interconnect layer 316 and the cathode layer 332. The conductive material 340, 342 serves to direct electrons from the anode layer 326 to the interconnect layer 316, and from the interconnect layer 316 to the cathode layer 332.

To effect a gas-tight seal between the cells 312, 314 and the interconnect layer 316, sealing means in the form of a sealant are positioned therebetween. That is, a sealant 348 of a suitable composition such as devitrifying glass is formed between the interconnect layer 316 and two opposite edges of the second surface of the electrolyte 320 by placement of a bead of glass material thereabout. The bead is then heated to melt the material. The devitrified glass material has a melting point less than that of any other component of the cell and heating of the sealant to form the seal does not affect the electrode material. Upon cooling, the devitrifying glass turns to a glass/ceramic. Similar beads of devitrifying glass sealant 349, 350 are positioned between opposite edges of the first surface of the adjacent electrolyte layers 318, 320 and the interconnect layers 316, 317 and are heated and cooled to form a gas-tight seal. Alternatively, the seals 348, 349 and 350 can be composed of a suitable oxidation resistant metal braze alloy such as Ag/Pd. It is notable that the sealant 348 on the second surface of the interconnect 316 is positioned so that it is separated from the electron pathway of the interconnect layer 316. Likewise, the sealant 350 on the first surface of the interconnect layer 317 is separated from the electron pathway of interconnect layer 317.

Planar electrochemical cells can be produced by the following general procedure wherein the material for the cathode layer, anode layer, interconnect layer and electrolyte layer are chosen from any of the previously enumerated materials. Initially, a coating of conducting material such as LSCO is applied to both the first and second surfaces of the desired electrolyte layer. The cells are then fired at a temperature ranging from 1050° to about 1200° C. An intermediate coating of a mixture of LSCO and silver/palladium alloy is then placed on the LSCO coatings of the surfaces of each cell. A particularly suitable composition for the intermediate coating is about 75% LSCO to about 25% silver-palladium alloy. The ratio of silver to palladium in the alloy may vary, but a ratio of 70% to 30% is suitable. The intermediate coating is fired to both surfaces of the cells at a temperature ranging from 1050° to about 1200° C. Alternately, both coatings may be fired simultaneously. The cells are then joined face-to-face and in electrical series by attachment of the interconnect layers. The interconnect layers are attached to the cells by application of the devitrified glass which may be screen printed as a paste onto either the electrolyte plates or interconnects before assembly of the stack. The stacks are fired at a temperature ranging from 900° to about 1100° C.

In operation, an electrical voltage is applied across the end member interconnect layer at the top and bottom of the stack. The end member interconnect layer may have only one set of channels formed in their surfaces adjacent to the electrode layers. Electrons flow from the anode layer on the first surface of an electrolyte layer through the pathway of the interconnect layer to the cathode layer of the adjacent cell. When the series stacked planar system is used, for example, in the production or enrichment of oxygen gas, a feed stream such as air or a process off-gas is passed through the gas passages 300, 302. Electrons at the cathode layer ionize oxygen molecules to oxygen ions. The oxygen ions pass through the electrolyte layer via the influence of an applied voltage differential to the anode layer where the electrons are given up and oxygen molecules are formed inside the gas passages 322, 324. The electrons given up at the anode layer continue to travel through the interconnect layer to the cathode layer of an adjacent cell where the process continues at that cell.

The dimension of the gas passages formed in the interconnect layer may be optimized for specific functions and operating conditions of the stack of planar cells. For example, in a deoxygenating application when the feed gas contains <5% $O_2$ and the objective is to remove oxygen from the stream to a level of <1 ppm, the depth of the gas passages 300, 302 may be reduced to minimize the diffusion path length of oxygen to the cathode surface. In this instance, the depth can be <1 mm, while the width and spacing of the passages are set by considerations of pressure drop through the gas passages, the electrical sheet resistance of the cathode and the mechanical strength of the cell assembly. The gas passages may contain additional ribs, static mixers and other features to minimize gas phase diffusion resistance.

The gas passages may be fabricated within the interconnect layer in a wide variety of shapes, in cross-section, such as rectangular, trapezoidal, semi-circular and the like. The depth and spacing of the passages may be widely varied and optimum designs may be assessed for a given application without undue experimentation. For example, the depth of a passage may decrease with distance traversed across the surface of the electrode layer in order to increase the diffusional flux to the electrode surface of the component gas being transported through the electrolyte. In an alternate embodiment, (not illustrated) the individual gas passages shown in FIG. 11 may be partially or totally replaced by means for minimizing gas phase diffusion resistance. A suitable means comprises a repeating network of isolated cylindrical, conical or rectangular pins, designed to distribute gas flow while minimizing pressure drop during operation.

Figure 12:
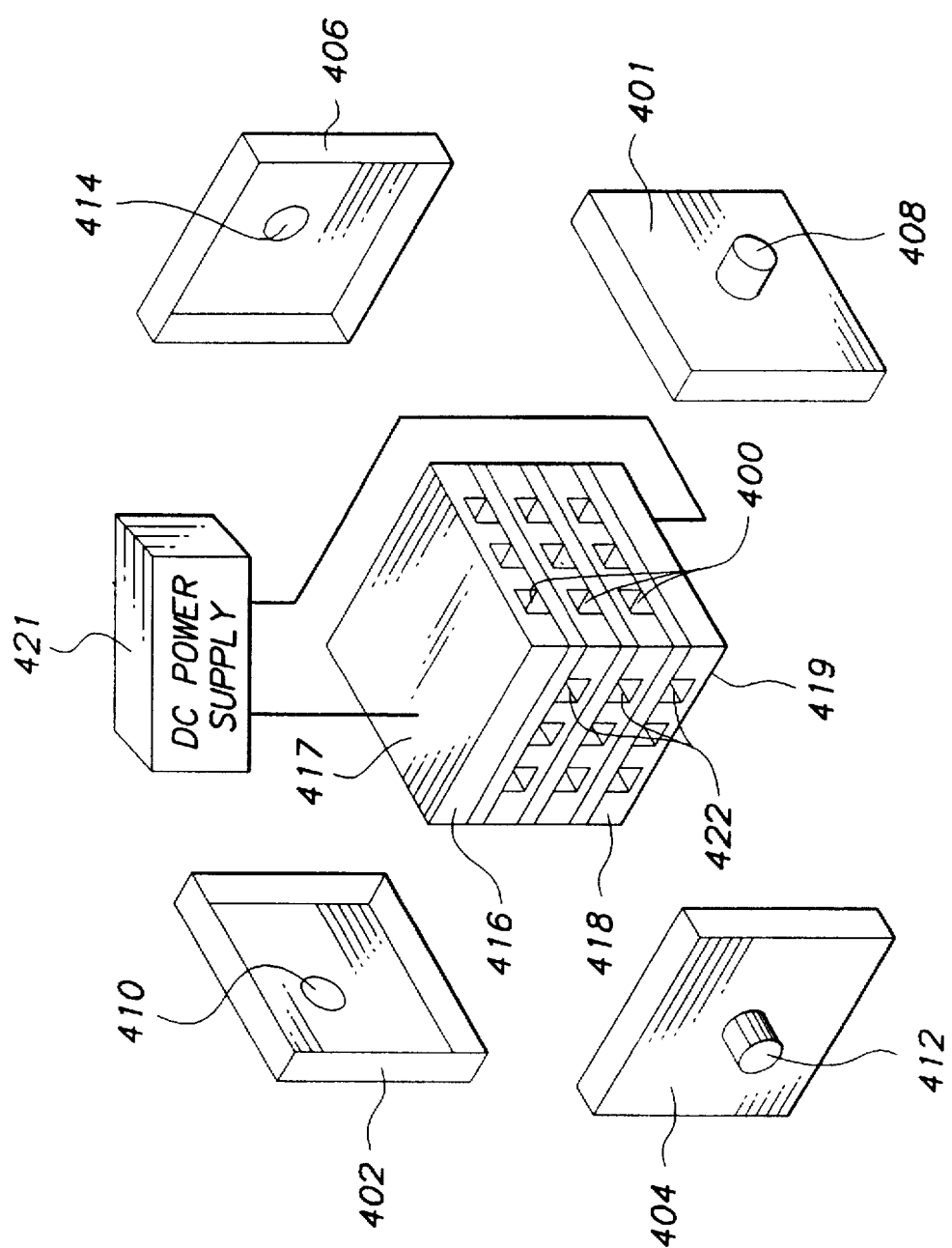
FIG. 12 further illustrates the electrochemical structure according to FIG. 11 wherein the cells are manifolded to capture product formed during operation.

A plurality of planar electrolytic cells can be joined in series to another plurality of planar cells to provide an integrated system of interconnected electrolytic cells as depicted in FIG. 12. Oxygen-containing gas feed may be introduced into the gas passages 400 via feed inlet 408 of manifold 401 and oxygen depleted gas is then withdrawn from the feed outlet 410 of manifold 402. The separated oxygen exuding from the gas passages 422 may be collected by manifolds 404, 406 attached to faces of the stack perpendicular to the manifolds 401, 402 and exits via outlets 412 and 414. The manifolds are sealed to the faces of the stacks to prevent short-circuitry of adjacent cells, for example, with an electrically insulating devitrified or glassy sealant A direct current or rectified alternating current power supply 421 is connected across the end-member interconnects 416 and 418. When oxygen is being transported through the electrolyte, the negative terminal of the power supply is connected to the end cathode interconnect layer 416 (via an optional end plate or coating 417) and the positive terminal is connected to the end anode interconnect layer 418 (also via optional end plate or coating 419). A sufficient voltage is applied across the stacks to drive current through the stacks causing the oxygen separation process to occur.

Figure 13:
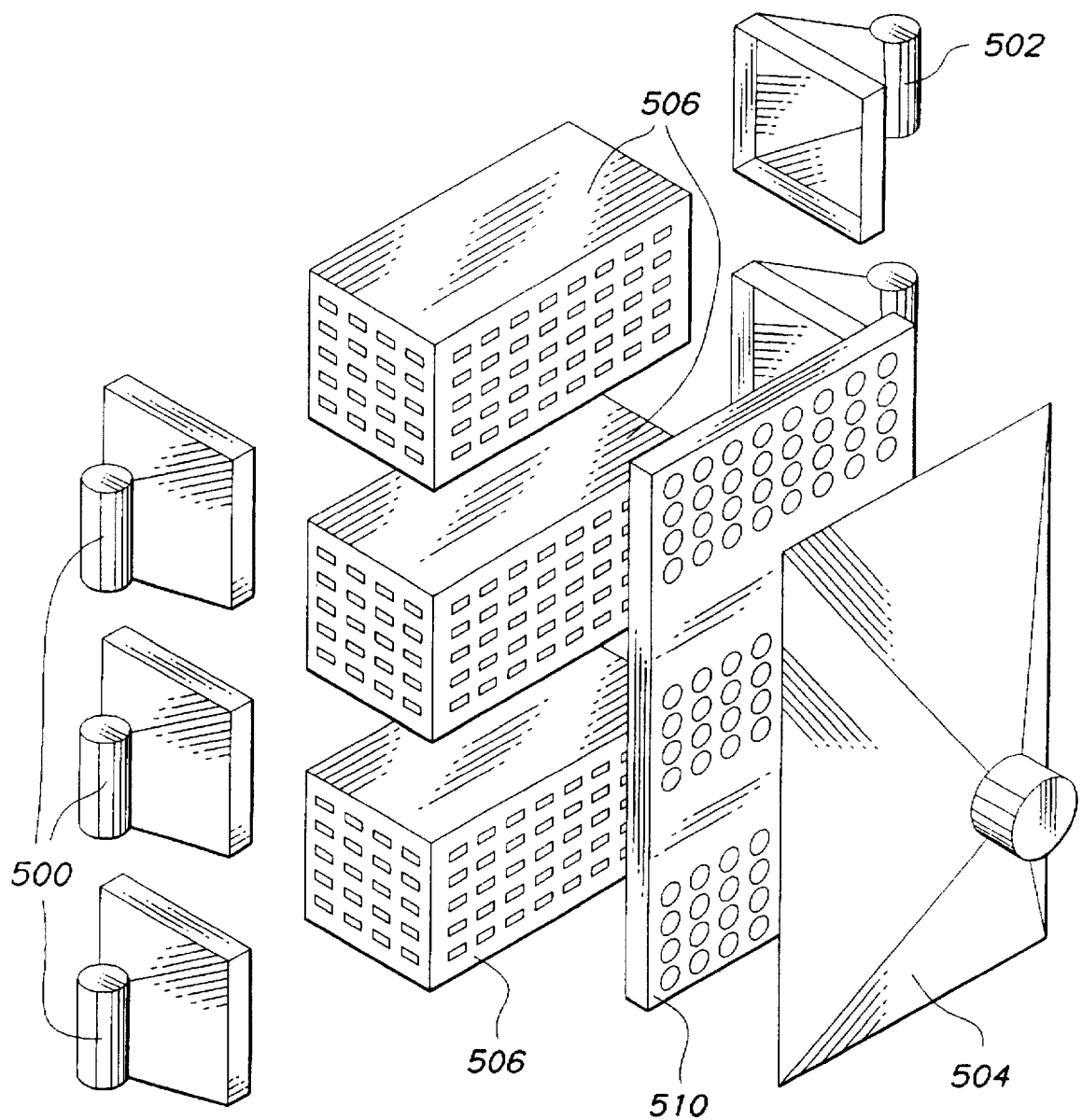
FIG. 13 illustrates an alternative embodiment for separating oxygen from air which employs a plurality of stacks connected pneumatically in parallel via collection manifolds.

In an alternative embodiment, for example, to separate oxygen from air, a plurality of stacks 506 may be connected pneumatically in parallel via their oxygen collection manifolds 500, 502 as illustrated in FIG. 13. The stacks may be mounted in a common air feed plenum 504, further equipped with a gas distributor plate 510, the spaces between the individual stacks being filled with an inert insulation (not shown). Electrical connection between stacks may be either in series or parallel configurations, or a combination thereof as is conventional in the art.

When the electrochemical device is operated to remove oxygen from an oxygen-containing gaseous mixture, such mixture is introduced into the stacks in parallel via manifold 500 and an oxygen depleted gaseous mixture is collected via manifolds 502. The oxygen removed during operation of the device is collected via plenum 504. Alternately, the manifolds may be configured such that the oxygen-containing gaseous mixtures passes through alternating stacks in a series flow configuration.

The electrochemical device of the present invention provides an interconnected series of planar electrolytic cells which maintains electrical and pneumatic integrity during operation. The configuration of the interconnect and the placement of sealant provides a gastight barrier between the internal and external environments of the electrolytic cells while avoiding deterioration or corrosion of the seal due to high operating temperatures. Many modifications of the basic illustrated planar embodiment may be made without departing from the spirit and scope of the invention as recited by the claims.

We claim:

1. An electrochemical solid-state device for transporting ions through an electrolyte comprising: a plurality of planar electrolytic cells connected in series by an electrically conductive interconnect layer and a sealing means to form a gas-tight seal therebetween, each electrolytic cell comprising an ion conducting electrolyte layer, a first electrode layer situated contiguous to a first surface of the electrolyte layer and a second electrode layer situated contiguous to a second surface of the electrolyte layer; a first surface of the interconnect layer comprising at least one gas passage for receiving a feedstream containing a component capable of being transported ionically through the electrolyte, which first surface of the interconnect layer is connected to the second electrode layer of a first planar electrolytic cell and a second surface of the interconnect layer which is connected to the first electrode layer of a second planar electrolytic cell, the second surface of the interconnect layer comprising at least one gas passage for withdrawing the component being transferred through the electrolyte layer, wherein a means for reducing gas phase diffusion resistance is attached to the first and second surfaces of the interconnect layer of each respective electrolytic cell which project into the gas passage, the interconnect layer further providing a pathway for movement of electrons between the first electrode layer of the second planar electrolytic cell and the second electrode layer of the first planar electrolytic cell.

2. The electrochemical device according to claim 1 where the gas passage on the first surface of the electrically conductive interconnect layer of each respective electrolytic cell are aligned substantially perpendicular to the gas passage on the second surface of the electrically conductive interconnect layer.

3. The electrochemical device according to claim 2 wherein the sealing means is selected from the group consisting of devitrified glass, glass, glass-ceramic composites, glass-metal composites, and oxidation resistant metal alloys and brazes.

4. The electrochemical device according to claim 1 wherein the means for minimizing gas phase diffusion resistance comprises pins, ribs or static mixers.

5. The electrochemical device according to claim 1 wherein the ion conducting electrolyte layer of each planar electrolytic cell is independently selected from a multicomponent ionic conducting metallic oxide comprising an oxide of at least two different metals or a mixture of at least two different metal oxides.

6. The electrochemical device according to claim 5 wherein the multicomponent ionic conducting metallic oxide is represented by the formula $A_xA'_{x'}A''_{x''}O_z$, where A,A',A" may be independently selected from Groups 2, 3, 13, 14, and 15, the F block lanthanides and the D block transition metals according to the Periodic Table of the Elements adopted by the IUPAC wherein $0<x\leq 1$, $0<x'\leq 1$, $0\leq x''\leq 1$, $x+x'+x''=1$ and z is a number which renders the compound charge neutral.

7. The electrochemical device according to claim 6 wherein the multicomponent ionic conducting metallic oxide is selected from the group consisting of calcia-doped ceria, yttria-doped ceria, strontia-doped ceria, yttria-magnesia-doped zirconia, yttria-doped zirconia, bismuth-vanadium oxide, ceria and hafnia.

8. The electrochemical device according to claim 2 wherein the anode layer and the cathode layer of each respective planar electrolytic cell independently comprise a multicomponent mixed conducting oxide.

9. The electrochemical device according to claim 8 wherein the multicomponent mixed conducting oxide is represented by the formula $A_xA'_{x'}A''_{x''}B_yB'_{y'}B''_{y''}O_z$, where A,A',A" are chosen from the group comprising Groups 1, 2 and 3 and the F block lanthanides; and B,B',B" are chosen from the D block transition metals according to the Periodic Table of the Elements adopted by the IUPAC wherein $0<x\leq 1$, $0\leq x'\leq 1$, $0\leq x''\leq 1$, $0\leq y\leq 1$, $0\leq y'\leq 1$, $0\leq y''\leq 1$, $x+x'+x''=1$, $y+y'+y''=1$ and z is a number which renders the compound charge neutral.

10. The electrochemical device according to claim 9 wherein the multicomponent mixed conducting oxide is selected from the group consisting of lanthanum strontium cobaltite, lanthanum strontium cobalt ferrite, lanthanum barium cobaltite, lanthanum barium cobalt ferrite and strontium cobalt ferrite.

11. The electrochemical device according to claim 1 wherein the anode layer and the cathode layer of each respective planar electrolytic cell independently comprise a metal or alloy.

12. The electrochemical device according to claim 11 wherein the anode layer and the cathode layer of each respective planar electrolytic cell contain silver.

13. The electrochemical device according to claim 1 wherein the electrically conductive interconnect layer comprises an oxidation-resistant metal or an alloy.

14. The electrochemical device according to claim 1 wherein the electrically conductive interconnect layer of each respective planar electrolytic cell comprises a multicomponent electronically conductive metallic oxide.

15. The electrochemical device according to claim 14 wherein the multicomponent electronically conductive metallic oxide is selected from the group consisting of lanthanum strontium manganite, lanthanum strontium chromite and lanthanum calcium manganite and lanthanum calcium chromite.

* * * * *